(12) United States Patent
Cho et al.

(10) Patent No.: US 8,202,514 B2
(45) Date of Patent: Jun. 19, 2012

(54) BACILLUS SUBTILIS STRAIN HAVING ANTAGONISTIC ACTIVITY FOR CONTROLLING PLANT DISEASES

(75) Inventors: Kwang Yun Cho, Daejeon (KR); Jin-Cheol Kim, Daejeon (KR); Gyung Ja Choi, Daejeon (KR); Seon-Woo Lee, Daejeon (KR); Yong Ho Choi, Daejeon (KR); Kyoung Soo Jang, Daejeon (KR); He Kyoung Lim, Daejeon (KR)

(73) Assignee: Korea Research Institute of Chemical Technology (KR)

( * ) Notice: Subject to any disclaimer, the term of this patent is extended or adjusted under 35 U.S.C. 154(b) by 1625 days.

(21) Appl. No.: 10/592,747

(22) PCT Filed: Mar. 23, 2005

(86) PCT No.: PCT/KR2005/000842
§ 371 (c)(1),
(2), (4) Date: Sep. 13, 2006

(87) PCT Pub. No.: WO2005/090553
PCT Pub. Date: Sep. 29, 2005

(65) Prior Publication Data
US 2011/0262416 A1 Oct. 27, 2011

(30) Foreign Application Priority Data

Mar. 24, 2004 (KR) .................. 10-2004-0020074

(51) Int. Cl.
*A01N 63/00* (2006.01)
*A61K 39/07* (2006.01)
(52) U.S. Cl. .................. 424/93.462; 424/246.1
(58) Field of Classification Search .................. None
See application file for complete search history.

(56) References Cited

U.S. PATENT DOCUMENTS
6,291,426 B1 * 9/2001 Heins et al. .................. 514/2.9
* cited by examiner

*Primary Examiner* — Chris R Tate
*Assistant Examiner* — Douglas F White
(74) *Attorney, Agent, or Firm* — Baker & Hostetler LLP

(57) ABSTRACT

A novel strain of *Bacillus subtilis* EB120 shows high antagonistic activity for controlling various plant diseases including barley powdery mildew, cucumber powdery mildew, red pepper anthracnose, rice blast, tomato gray mold, tomato late blight and wheat leaf rust, it can be effectively used as a microbioside for biologically controlling the plant diseases.

5 Claims, 3 Drawing Sheets

BACILLUS SUBTILIS STRAIN HAVING ANTAGONISTIC ACTIVITY FOR CONTROLLING PLANT DISEASES

FIELD OF THE INVENTION

The present invention relates to a novel *Bacillus subtilis* strain having antagonistic activity against plant diseases; a microbial agent for controlling plant diseases comprising the same; and a method for biologically controlling plant diseases using the same.

BACKGROUND OF THE INVENTION

Since crop yield decreases by as much as 30% to 100% in case of cultivating crops without pesticides, it is essential to use the pesticides for improving crop yield. However, improper use of synthetic chemical pesticides in crop production causes several problems such as nonselective toxicity, accumulation of toxic compounds and outbreak of pathogens resistant to the pesticides. One way to handle these problems is to develop biopesticides using antagonistic microorganisms. Biopesticides are roughly classified into plant extracts, microorganisms, natural enemies, natural bioactive substances and genetically modified organisms (GMO). Biopesticides can be safer, more biodegradable, and less expensive to develop than synthetic chemical pesticides.

The study on the development of biopesticides, especially microbial fungicides, has been a major interest in the field of plant pathology, and has been actively carried out for the past 70 years, resulting in more than 40 microbial fungicide products in last ten years.

Meanwhile, *Bacillus* sp. is a Gram-positive bacterium abundant in soil and is almost as widely researched and commercialized as *Pseudomonas* Genus. *Bacillus* sp. produces biologically active secondary metabolites and forms thermostable endospores tolerant to bad conditions. Gustafson Inc. developed a microbial fungicide employing *Bacillus subtilis* for treating furrows and seeds of cotton and peanut, and it has been sold on the market under a commercial name of Kodiak (Backman et al., *Improving Plant Productivity with Rhizosphere Bacteria* 3-8, 1994). Further, a microbial fungicide using a mixture of *Bacillus subtilis* and *Bacillus amyloliquefaciens* has been introduced into the market in 2001 under a commercial name of BioYield. Numerous *Bacillus* sp. strains have been used for increasing crop yield in China. In addition, Bayer Inc. developed an agent for controlling soil communicable diseases comprising *Bacillus* FZB 24, and Taensa Inc. produced a microbial fungicide using the same.

Furthermore, AgraQuest Inc. developed Serenade, a microbial fungicide using *Bacillus subtilis* QST713. Unlike others using the above-mentioned *Bacillus* sp. strains, this microbial fungicide is effective against over 40 plant diseases including gray mold, damping-off and powdery mildew. It has been reported that this antagonistic microorganism effectively controls various kinds of plant diseases through several mechanisms such as competition, parasitism, antibiosis and induced resistance, and produces more than 30 kinds of lipopeptides as antibiotic compounds including three groups of iturins, plipastins and surfactins (Ritter, *Chemical & Engineering News* 81: 30-35, 2003).

In Korea, the study for biologically controlling postharvest root rots of ginseng began in the early 1970, followed by the study for biological control of the red pepper blight, *Fusarium* wilt of cucumber and strawberry, sesame damping-off and gray mold. However, the study has been unsuccessful due to the instability in the result, difficulty in formulation, poor productivity and so on. The first domestic microbial fungicide using a *Bacillus* sp. strain is Topseed developed by Greenbiotech Co., Ltd. However, since it has been shown to be effective only against powdery mildew, its application has been quite limited.

The present inventors have endeavored to develop a new microbial fungicide having potent antifungal activity against a wide range of plant diseases, and have found that a plant endophytic bacterium, *Bacillus subtilis* EB120 isolated from red peppers shows antagonistic activity against several kinds of plant diseases including powdery mildew of barley and cucumber, red pepper anthracnose, rice blast, tomato gray mold, tomato late blight and wheat leaf rust.

SUMMARY OF THE INVENTION

Accordingly, it is an object of the present invention to provide a novel strain of *Bacillus subtilis* having antagonistic activity for controlling plant diseases.

It is another object of the present invention to provide a microbial agent for controlling plant diseases comprising the strain.

It is a further object of the present invention to provide a method for controlling plant diseases using the microbial agent.

In accordance with one aspect of the present invention, there is provided a novel strain of *Bacillus subtilis*, EB120 (KCTC 10578BP) having antagonistic activity for controlling plant diseases.

In accordance with another aspect of the present invention, there is provided a microbial agent for controlling plant diseases comprising the strain or antagonistically active substances derived therefrom as effective ingredients.

In accordance with a further aspect of the present invention, there is provided a method for controlling plant diseases comprising the step of applying an effective amount of the microbial agent to plants.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

The present invention provides a novel strain of *Bacillus subtilis*, EB120(KCTC 10578BP), exhibiting broad-spectrum antagonistic activity against plant diseases.

The novel strain of the present invention is isolated from red pepper leaves. Morphological and biochemical studies and 16S rDNA nucleotide sequencing analysis reveal that this strain belongs to *Bacillus subtilis*. This novel strain was designated as *Bacillus subtilis* EB120 and was deposited on Jan.

6, 2004 with the Korean. Collection for Type Cultures (KCTC) (Address: Korea Research Institute of Bioscience and Biotechnology (KRIBB), #52, YuSong-ku; Taejon, 305-333, Republic of Korea) under the accession number KCTC 10578BP, in accordance with the terms of Budapest Treaty on the International Recognition of the Deposit of Microorganisms for the Purpose of Patent Procedure.

Figure 1:
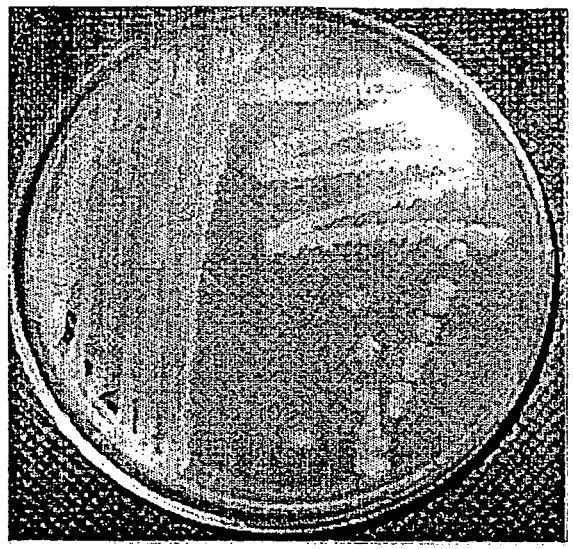
FIG. 1: a photograph of *Bacillus subtilis* EB120 cultured in a tryptic soy agar medium.

*Bacillus subtilis* EB120 of the present invention shows the following morphological and biochemical characteristics: it grows with thinly spreading onto a tryptic soy agar medium, and its single colony is of a small snowflower shape (see FIG. 1). Further, *Bacillus subtilis* EB120 belongs to *Bacillus* sp. which shows positive reactions in Gram staining, KOH test, catalase and oxidase tests; forms thermostable endospores; and is capable of hydrolyzing starch and casein. Furthermore, except for the case of maltotriose, *Bacillus subtilis* EB120 and ATCC 6051 exhibit same preferences for sugars.

Further, 16S rDNA nucleotide sequencing analysis shows that *Bacillus subtilis* EB120 has the nucleotide sequence of SEQ ID No: 1 which has 99% of sequence homology to that of *Bacillus subtilis*.

*Bacillus subtilis* EB120 thus characterized shows broad and high antagonistic activity far controlling plant diseases including barley powdery mildew, cucumber powdery mildew, red pepper anthracnose, rice blast, tomato gray mold, tomato late blight and wheat leaf rust.

Thus, *Bacillus subtilis* EB120 of the present invention can be employed as a microbial agent for controlling plant diseases. The strain alone may serve as such microbial agent. Or the microbial agent may be prepared by mixing suitable carriers with a whole broth culture of the strain, a solvent extract obtained therefrom or a single endospore, and then formulating the mixture into powders, pellets, granules or solutions. The carriers employable in the present invention include, but are not limited to, water, white carbon and kaolin.

The microbial agent of the present invention can be useful in preventing growth inhibition and withering of the plant caused by plant pathogens when applied with an effective amount thereof either to soil where the plants grow or to the plants themselves.

*Bacillus subtilis* EB120 is applied to target plants at a cell concentration of $1.0 \times 10^4$ cells/ml to $1.0 \times 10^{10}$ cells/ml, preferably $1.0 \times 10^6$ cells/ml to $1.0 \times 10^9$ cells/ml.

The following Examples are intended to further illustrate the present invention without limiting its scope.

EXAMPLE 1

Isolation of *Bacillus subtilis* EB120

5 g of fresh red pepper leaves were soaked in 2% NaOCl supplemented with 0.1% Tween 20 for 10 sec to sterilize their surfaces. The leaves thus sterilized were mixed with 45 ml of sterile distilled water in a mortar and the mixture was ground with a pestle, 1 ml of aliquot was taken from the ground mixture and diluted with sterile distilled water at a ratio of 1:10, 1:100 and 1:1000, respectively. 200 µl of each diluent was spread onto a tryptic soy agar medium supplemented with 40 µg/ml of cycloheximide and incubated at 30° C. until a bacterial colony was formed. The colony was taken from the medium, inoculated into a fresh nutrient agar medium and subjected to three to four times of subculture, to isolate a pure culture of a bacterial strain.

EXAMPLE 2

Characterization of *Bacillus subtilis* EB120

The bacterial strain isolated in Example 1 was identified based on characterization of morphological and biochemical features and 16S rDNA nucleotide sequencing.

(1) Morphological and Biochemical Characteristics

The isolated strain grew with thinly spreading onto a tryptic soy agar medium, and its single colony formed a small snowflower shape (FIG. 1). It showed positive reactions in Gram staining and KOH tests, which suggest it belongs to *Bacillus* sp.; exhibited positive reactions in catalase and oxidase tests; formed thermostable endospores; and was capable of hydrolyzing starch and casein. Further, its carbon utilization activity was assessed using a GN2 microplate (Biolog, Inc.) and the results are shown in Table 1. Here, *Bacillus subtilis* subsp. *subtilis* ATCC6051 strain (Korean Collection for Type Cultures, Korea Research Institute of Bioscience and Biotechnology) was employed as a control strain.

TABLE 1

| Sugar | EB120 strain | ATCC 6051 strain |
|---|---|---|
| L-arabinose | − | − |
| Arabitol | − | − |
| Albutin | + | + |
| Cellobiose | + | + |
| D-fructose | + | + |
| L-fructose | − | − |
| D-galaturonic acid | − | − |
| α-D-glucose | + | + |
| A-D-lactose | − | − |
| Maltotriose | − | + |
| D-mannitol | + | + |
| D-mannose | + | + |
| D-melezitose | − | − |
| D-melibiose | − | − |
| α-methyl-D-galactoside | − | − |
| β-methyl-D-galactoside | − | − |
| α-methyl-D-mannoside | − | − |
| D-psicose | + | + |
| L-rhamnose | − | − |
| Sedoheptulosan | − | − |
| Stachyose | − | − |
| Sucrose | + | + |
| D-tagatose | − | − |
| D-trehalose | + | + |
| Xylitol | − | − |
| D-xylose | − | − |

As can be seen in Table 1, except for the case of maltotriose, *Bacillus subtilis* EB120 and ATCC 6051 exhibit same preferences for sugars. That is, the both strains utilized albutin, cellobiose, D-fructose, α-D-glucose, D-mannitol, D-mannose, D-psicose, sucrose and D-trehalose. However, while the control strain, *Bacillus subtilis* subsp. *subtilis* ATCC6051 utilized maltotriose, the isolated strain of the present invention did not.

(2) 16S rDNA Nucleotide Sequencing 16S rDNA nucleotide sequencing analysis revealed that the isolated strain had the nucleotide sequence of SEQ ID No: 1 which shows 99% of sequence homology to that of *Bacillus subtilis*.

These results demonstrate that the isolated strain is a novel strain of *Bacillus subtilis*. This novel strain was designated as *Bacillus subtilis* EB120 and deposited on Jan. 6, 2004 with the Korean Collection for Type Cultures (KCTC) (Address: Korea Research Institute of Bioscience and Biotechnology (KRIBB), #52, Oun-dong, Yusong-ku, Taejon, 305-333, Republic of Korea) under the accession number KCTC 10578BP.

EXAMPLE 3

Test for Pesticidal Activity of *Bacillus subtilis* EB120 Against Plant Diseases In order to examine in vivo antifungal activity of *Bacillus subtilis* EB120 (hereinafter, referred to as "EB120") against tomato gray mold, tomato late blight, cucumber anthracnose and then barley powdery mildew, target plants were treated with EB120 and plant pathogens were inoculated thereto 24 hrs later.

Specifically, EB120 was inoculated into 200 ml of a sterilized tryptic soy broth (Becton and Dickinson) and cultured at 30° C. for 3 days with shaking at 150 rpm. After the culture solution was diluted with distilled water at a ratio of 1:3 and 1:9, 30 ml each of the culture solution and diluents was mixed with 100 µg/ml of Xanthan gum. Tomatoes, barleys and cucumbers were cultivated in plastic ports filled with gardening bedsoil to about 70% of volume under a greenhouse condition (25±5° C.) for 1 to 3 weeks until they reached to the $2^{nd}$ leaf stage of tomatoes, the $1^{st}$ leaf stage of barleys and the $2^{nd}$ leaf stage of cucumbers, respectively. They were treated with each of the mixtures, respectively, allowed to dry in air, and kept at room temperature for 24 hrs.

Sequentially, infestation with each pathogen to target plants was conducted as follows. Tomato late blight and gray mold were induced by spraying a zoospore suspension released from sporangia ($5 \times 10^4$ sporangia/ml) of a late blight pathogen, *Phytophthora infestans* (Kangnung National University) and a spore suspension ($5 \times 10^5$ spores/ml) of gray mold pathogen, *Bouytis cinerea* (Korea Research Institute of Chemical Technology) to leaves of the $2^{nd}$ leaf stage of tomato seedlings, respectively, and growing the plants at 20° C. in a humid condition. Cucumbers were infested with an anthracnose pathogen by the following steps of spraying a spore suspension ($1 \times 10^6$ spores/ml) of *Colletotrichum orbiculare* (National Institute of Agricultural Science and Technology) to leaves of the $2^{nd}$ leaf stage of cucumber seedlings and growing the plants at 25° C. for 3 days in a constant temperature and humidity chamber after keeping them in a humid condition for 2 days. For infestation of barley powdery mildew, spores of a powdery mildew pathogen, *Blumeria graminis* f. sp. *hordei* (Korea Research Institute of Chemical Technology) subcultured from host plants were inoculated into leaves of the $1^{st}$ leaf stage of barley seedlings and the plants were grown at 20° C. in a growth chamber.

A control group was treated with only 30 ml of a Xanthan gum solution (100 µg/ml) having no exposure to a EB120 culture solution, and a comparative group of the corresponding plant was treated with chlrothalonil (Sungbo Chemicals Co., Ltd.) for tomato late blight, dithianon (Hankook Samgong Co., Ltd.) for tomato gray mold, dichlofluanid (Dongbu Hannong Chemical Co., Ltd.) for cucumber anthracnose and benomyl (Dongyang Chemical Industry Co., Ltd.) for barley powdery mildew, respectively.

Disease severity of barley powdery mildew, cucumber anthracnose, tomato gray mold and tomato late blight were determined by visual estimation of the percentage area of leaves by sporulating lesions or the percentage of chlorotic and necrotic symptoms on the inoculated foliage at 7, 5, 3 and 4 days after the inoculation of pathogens, respectively. Percentage fungal control (control value) was calculated by way of Formula 1, and the results are shown in Table 2.

$$\text{Control value (\%)} = (ID_{UCG} - ID_{TEG}) \div ID_{UG} \times 100 \qquad \text{<Formula 1>}$$

wherein, $ID_{UCG}$ means an infestation degree of the untreated control group, and $ID_{TEG}$, an infestation degree of the treated experimental group.

TABLE 2

| Sample | Dilution ratio and concentration (µg/ml) | Tomato late blight | Cucumber anthracnose | Tomato gray mold | Barley powdery mildew |
|---|---|---|---|---|---|
| *Bacillus* | Undiluted | 88 | 3 | 95 | 82 |
| *subtilis* | 1:3 diluent | 13 | 3 | 50 | 72 |
| EB120 | 1:9 diluent | 0 | 3 | 23 | 58 |
| Chlro- | 100 µg/ml | 100 | | | |
| thalonil | 50 µg/ml | 89 | | | |
| Dithianon | 100 µg/ml | | 100 | | |
| | 10 µg/ml | | 80 | | |
| Dichlo- | 80 µg/ml | | | 97 | |
| fluanid | 40 µg/ml | | | 86 | |
| Benomyl | 100 µg/ml | | | | 100 |
| | 1 µg/ml | | | | 52 |

As shown in Table 2, it has been found that EB120 exhibits high in vivo antifungal activity against tomato late blight, tomato gray mold and barley powdery mildew.

EXAMPLE 4

Selection of Optimal Medium for Maximizing Antagonistic Activity of *Bacillus subtilis* EB120 Against Plant Diseases In order to select an optimal medium for producing metabolites having antifungal activity from *Bacillus subtilis* EB120, cultural experiments using several kinds of media were carried out as follows.

EB120 was inoculated into 6 kinds of broths listed in Table 3 and cultured at 30° C. for 3 days with shaking at 150 rpm. The culture solution was diluted with distilled water at a ratio of 1:3 and 1:9. Xanthan gum was added to each diluent at a concentration of 100 µg/ml, barleys were infested with a powdery mildew pathogen according to the same method as described in Example 3, and effect on controlling the plant disease was determined. The results are summarized in Table 3.

TABLE 3

| | Control value (%) | |
|---|---|---|
| Medium | 1:3 diluent | 1:9 diluent |
| Nutrient broth | 10 | 10 |
| Tryptic soy broth | 70 | 52 |
| Potato dextrose broth | 46 | 0 |
| Proteose peptone glucose sucrose broth | 40 | 20 |
| Glucose starch broth | 52 | 10 |
| Glucose peptone broth | 40 | 20 |
| M523 broth | 30 | 10 |

As can be seen in Table 3, the antifungal activity of *Bacillus subtilis* EB120 against barley powdery mildew was highest in case of culturing it in a tryptic soy broth.

EXAMPLE 5

In Vivo Antifungal Activity of *Bacillus subtilis* EB120 Against Cucumber Powdery Mildew EB120 was inoculated into a tryptic soy broth and cultured at 30° C. for 3 days with shaking at 150 rpm. The culture solution was diluted with distilled water at a ratio of 1:10, 1:25, 1:50, 1:100 and 1:200. Each diluent was mixed with 250 µg/ml of Tween 20, and sprayed to leaves of the $7^{th}$ leaf stage of cucumbers.

Topseed (Greenbiotech Co., Ltd.) known as a microbial fungicide for controlling powdery mildew was diluted with distilled water at a ratio of 1:10, 1:25, 1:50, 1:100 and 1:200, and each diluent and flusilazole (Dongbu Hannong Chemical Co., Ltd.) as a positive control were sprayed to cucumber plants to prepare a comparative group. The cucumbers treated with Tween 20 solution alone were employed as a control group.

1 week after spraying, each diluent of the culture solution and comparative sample was sprayed to the target cucumbers second time. 1 week after further spraying, effect on controlling powdery mildew was assessed according to the same method as described in Example 3. The cucumbers were allowed to be infested naturally from a resident powdery mildew pathogen, *Sphaerotheca fidigenea* in a greenhouse.

The above experimental procedure was repeated twice and results are shown in Table 4.

TABLE 4

| Sample | Dilution ratio and concentration (μg/ml) | Control value (%) | |
|---|---|---|---|
| | | The 1$^{st}$ Exp. | The 2$^{nd}$ Exp. |
| *Bacillus* | 1:10 diluent | 86 ± 5.8 | 94 ± 3.3 |
| *subtilis* | 1:25 diluent | 84 ± 5.0 | 91 ± 2.7 |
| EB120 | 1:50 diluent | 76 ± 11 | 86 ± 3.0 |
| | 1:100 diluent | 21 ± 9.2 | 84 ± 6.7 |
| | 1:200 diluent | 16 ± 5.8 | 72 ± 20 |
| Topseed | 1:10 diluent | 87 ± 3.8 | 92 ± 5.4 |
| | 1:25 diluent | 60 ± 7.8 | 82 ± 6.7 |
| | 1:50 diluent | 56 ± 9.3 | 48 ± 11 |
| | 1:100 diluent | 32 ± 23 | 14 ± 39 |
| | 1:200 diluent | 26 ± 13 | 45 ± 20 |
| Flusilazole | 10 μg/ml | 97 | 97 |
| | 30 μg/ml | 99 | 99 |

Figure 2:
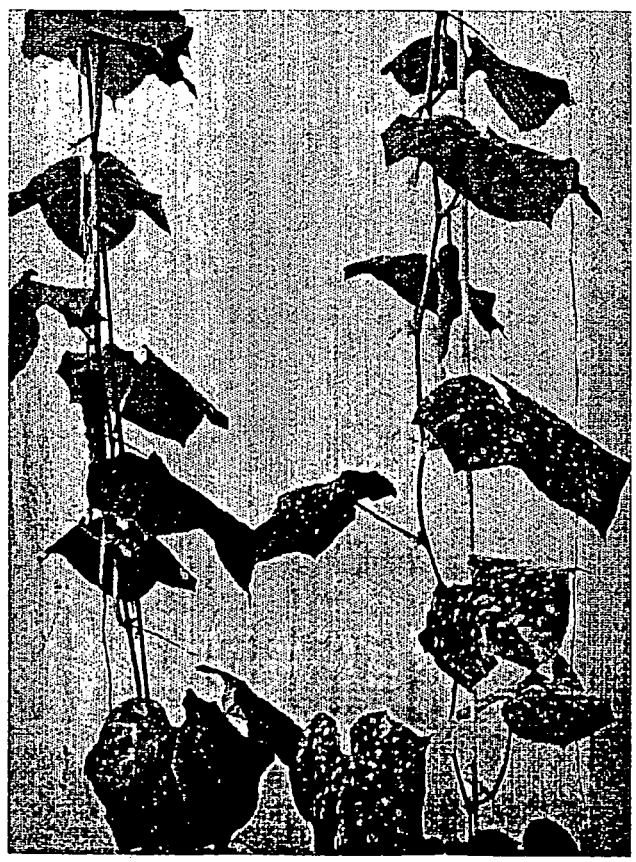
FIG. 2: a photograph showing in vivo antifungal activity of *Bacillus subtilis* EB120 against cucumber powdery mildew.

As illustrated in Table 4, all the diluents of *Bacillus subtilis* EB120 broth culture showed high in vivo antifungal activity against cucumber powdery mildew, and even in case of using the 1:200 diluent, its disease control efficacy was meaningful. Further, as compared with Topseed, the experimental groups treated with 1:50 or lower diluents showed equivalent or higher in vivo antifungal activity than the Topseed treatment group. FIG. 2 shows in vivo antifungal activity of *Bacillus subtilis* EB120 against cucumber powdery mildew. While the control group treated with Tween 20 solution alone showed typical lesions of powdery mildew, there was little lesion in the cucumber leaves of the experimental groups treated with the diluents of *Bacillus subtilis* EB120 broth culture.

EXAMPLE 6

Test for In Vivo Antifungal Activity of *Bacillus subtilis* EB120 Culture Solution, Ethylacetate and Butanol Extracts Thereof Against Plant Diseases In order to estimate antifungal activity of substances produced by the *Bacillus subtilis* EB120, a whole broth culture of *Bacillus subtilis* EB120, and ethylacetate and butanol extracts thereof were subjected to test for antifungal activity for controlling plant diseases, as follows.

EB120 was inoculated into a tryptic soy broth, cultured at 30° C. for 3 days with shaking at 150 rpm, and subjected to centrifugation at 9,000 rpm for 12 min, to separate a supernatant. The supernatant was extracted with the equal volume of ethylacetate twice to obtain an ethylacetate extract, and the ethylacetate extract was concentrated under reduced pressure. A butanol extract was obtained from the supernatant according to the same method as described above except for using butanol as a solvent. After an extract sample corresponding to 40 ml of the culture solution was taken from each of the extracts, the ethylacetate extract sample was dissolved in 4 ml of acetone and the butanol extract sample was dissolved in 2 ml of methanol. Both solutions were diluted with Tween 20 solution (250 μg/ml) to give a final volume of 40 ml each. On the other hand, Tween 20 was added to 40 ml of the culture supernatant of EB120 at a concentration of 250 μg/ml.

Each solution was sprayed to red pepper, rice, tomato, wheat, and barley plants. 1 day after spraying, 7 kinds of plant pathogens causing red pepper anthracnose (PAN), rice blast (RCB), rice sheath blight (RSB), tomato gray mold (TGM), tomato late blight (TLB), wheat leaf rust (WLR) and barley powdery mildew (BPM), were inoculated thereto, respectively, and effect on controlling the plant diseases was assessed.

Infestations of tomato gray mold, tomato late blight, and barley powdery mildew were carried out according to the same method as described in Example 3.

Meanwhile, pregerminated red pepper seeds were sowed in a pot having a diameter of 7.0 cm and allowed to grow up to the 8$^{th}$ leaf stage in a greenhouse. A spore suspension ($5 \times 10^5$ spores/ml) of an anthracnose pathogen, *Colletotrichum coccodes* (Korea University), was sprayed onto leaves of the 8$^{th}$ leaf stage red peppers. The red peppers thus treated were kept in a humid condition for 2 days and incubated at 25° C. for 2 days in a chamber having steady temperature and humidity to induce red pepper anthracnose.

Rice blast was induced by spraying a spore suspension ($5 \times 10^5$ spores/ml) of a rice blast pathogen, *Magnaporthe grisea* (Seoul National University) to the 2$^{nd}$ leaf stage of rice seedlings, keeping the plants at 25° C. in a humid condition for 1 day, and incubating them at 25° C. for 5 days in a growth chamber.

Rice sheath blight was induced by the following steps of culturing *Thanatephorus cucumeris* (Korea Research Institute of Chemical Technology) in a medium (90 g of wheat bran, 15 g of rice bran, 100 ml of distilled water), inoculating the culture solution into the 3$^{rd}$ leaf stage of rice seedlings, keeping the plants at 25° C. in a humid condition for 4 days, and incubating them at 25° C. for 4 days in a growth chamber.

For infestation of wheat leaf rust, spores of a leaf rust pathogen, *Puccinia recondita* (Korea Research Institute of Chemical Technology) were suspended in Tween 20 (250 μg/ml) at a concentration of 0.67 g spore/l, and the suspension was sprayed to the 1$^{st}$ leaf stage of wheat seedlings. The plants were kept at 20° C. in a humid condition for 1 day and incubated at 20° C. for 6 days in a growth chamber.

Disease severity was determined 4 days after the pathogen inoculation for red pepper anthracnose; 5 days after that for rice blast; and 7 days after that for wheat leaf rust and rice sheath blight. Percentage fungal control (control value) was estimated according to the same method as described in Example 3. The results are shown in Table 5.

TABLE 5

| Sample | Control value (%) | | | | | | |
|---|---|---|---|---|---|---|---|
| | PAN | RCB | RSB | TGM | TLB | WLR | BPM |
| Culture supernatant | 93 | 83 | 0 | 94 | 94 | 90 | 92 |
| Ethylacetate extrat | 0 | 70 | 0 | 0 | 0 | 53 | 0 |
| Butanol extract | 96 | 98 | 60 | 94 | 95 | 83 | 93 |

As can be seen in Table 5, the ethylacetate extract of *Bacillus subtilis* EB120 culture supernatant had no effect on controlling the plant diseases including red pepper anthracnose, rice sheath blight, tomato gray mold, tomato late blight and barley powdery mildew, but the butanol extract thereof showed equivalent or higher antifungal activity against all the tested plant diseases than the culture supernatant of *Bacillus subtilis* EB120. These results suggest that the substances having antifungal activity produced by *Bacillus subtilis* EB120 have relatively high polarity.

EXAMPLE 7

Test for Thermostability of Metabolites Having Antifungal Activity Produced by *Bacillus subtilis* EB120

In order to examine thermostability of the metabolites having antifungal activity produced from *Bacillus subtilis* EB120, the culture supernatant and butanol extract thereof were heated to various temperature conditions, i.e., 4° C., room temperature, 30° C., 40° C., 50° C., 60° C., 70° C., 100° C. and 121° C., and then were treated to plant pathogens to assess inhibitory effect on mycelial growth of plant pathogenic fungi.

In particular, the EB120 culture supernatant and butanol extract obtained in Example 6 were pretreated by cooling them at 4° C. for 24 hrs; keeping them at room temperature for 24 hrs; keeping them at 30° C., 40° C., 50° C., 60° C. and 70° C. for 5 hrs; and keeping them at 100° C. and 121° C. for 15 min, respectively. The culture supernatant was diluted with distilled water at a ratio of 1:2, and the butanol extract was dissolved in methanol at a concentration of 200 mg/ml. 50 µl of each sample was dropped on a paper disk having a diameter of 8 mm, which was dried in the air thereafter. A rice blast pathogen, *Magnaporthe grisea* (Seoul National University) was inoculated into a dextrose agar medium according to a pour-plating method. The treated paper disk was transferred onto the dextrose agar plates inoculated with *Magnaporthe grisea* and then incubated at 25° C. for 3 days. Sequentially, inhibitory effect on hyphal growth was determined by measuring a diameter of inhibition zone surrounding each paper disk.

Figure 3:
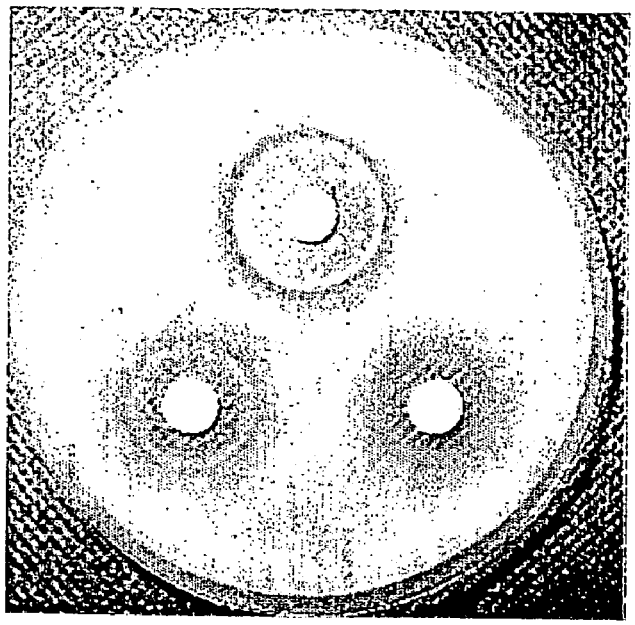
FIG. 3: a photograph showing inhibitory activity of a culture supernatant of *Bacillus subtilis* EB120 on growth of a rice blast pathogen.

As can be seen in FIG. 3, three regions having different patterns that are affected by metabolites produced from *Bacillus subtilis* EB120 were presented as follows: the region where the hyphal growth was completely inhibited (complete inhibition region); the region where an aerial hyphae didn't grow, but a hyphae grew only with penetrating into the medium (partial inhibition region); and the region where an aerial hyphae grew with looking as it adheres to the medium (aerial hyphae affected region). These results demonstrate that *Bacillus subtilis* EB120 produces at least three kinds or more of antifungal active metabolites.

Figure 4:
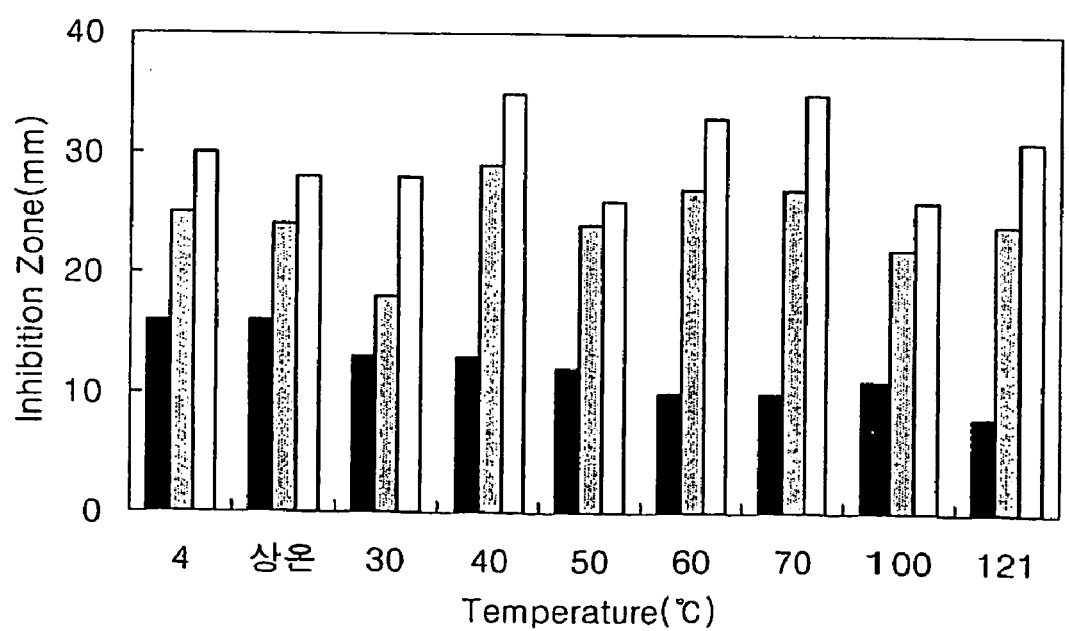
FIG. 4: a graph showing thermostability of a culture supernatant of *Bacillus subtilis* EB120.

It has been found that the antifungal metabolites produced by *Bacillus subtilis* EB120 show constant inhibitory activity on mycelial growth regardless of temperature (FIG. 4). These results suggest that the antifungal metabolites produced by *Bacillus subtilis* EB120 are relatively stable against heat. In FIG. 4, black bars represent the complete inhibition region; gray bars, the partial inhibition region; and white bars, the aerial hyphae affected region.

Figure 5:
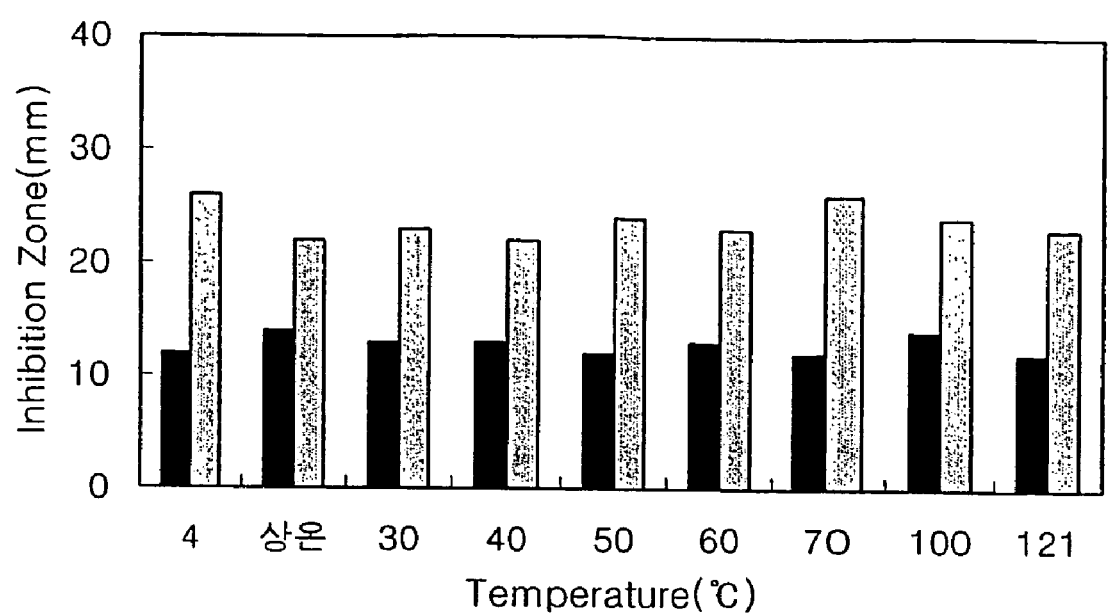
FIG. 5: a graph showing thermostability of a butanol extract obtained from a culture supernatant of *Bacillus subtilis* EB120.

Meanwhile, inhibitory effect of the butanol extract on the mycelial growth of *Magnaporthe grisea*, as a result of heat treatment was examined, and as it turned out, the butanol extract didn't show any aerial hyphae affected region unlike the culture supernatant. This result demonstrates that the antifungal active metabolite showing the pattern of aerial hyphae affected region is less polar than other antifungal metabolites showing different two patterns. Further, FIG. 5 shows that the butanol extract exhibits constant inhibitory activity on pathogen growth regardless of the heat treatment.

While the invention has been described with respect to the above specific embodiments, it should be recognized that various modifications and changes may be made to the invention by those skilled in the art which also fall within the scope of the invention as defined by the appended claims.

---

What is claimed is:

1. A biologically pure culture of the microorganism *Bacillus subtilis* EB120 (KCTC 10578BP) having antagonistic activity for controlling plant diseases.

2. A microbial agent for controlling plant diseases comprising the microorganism *Bacillus subtilis* EB120 (KCTC 10578BP) or a substance selected from the group consisting of a whole broth culture of the microorganism *Bacillus subtilis* EB120, a butanol extract of a supernatant of a whole broth culture of the microorganism *Bacillus subtilis* EB120, and spores of the microorganism *Bacillus subtilis* EB120 as an effective ingredient.

3. The microbial agent of claim 2, wherein the plant disease is selected from the group consisting of barley powdery mildew, cucumber powdery mildew, red pepper anthracnose, rice blast, tomato gray mold, tomato late blight, and wheat leaf rust.

4. A method for controlling plant diseases comprising the step of applying an effective amount of a biologically pure culture of the microorganism *Bacillus subtilis* EB120 (KCTC 10578BP), or a substance selected from the group consisting of a whole broth culture of the microorganism *Bacillus subtilis* EB120, a butanol extract of a supernatant of a whole broth culture of the microorganism *Bacillus subtilis* EB120, and spores of the microorganism *Bacillus subtilis* EB120, to one or more plants.

5. The method of claim 4, wherein the plant disease is selected from the group consisting of barley powdery mildew, cucumber powdery mildew, red pepper anthracnose, rice blast, tomato gray mold, tomato late blight and wheat leaf rust.

* * * * *

SEQUENCE LISTING

<160> NUMBER OF SEQ ID NOS: 1

<210> SEQ ID NO 1
<211> LENGTH: 1473
<212> TYPE: DNA
<213> ORGANISM: Bacillus subtilis

<400> SEQUENCE: 1

```
gacgaacgct ggcggcgtgc ctaatacatg caagtcgagc ggacagatgg gagcttgctc      60
cctgatgtta gcggcggacg ggtgagtaac acgtgggtaa cctgcctgta agactgggat     120
aactccggga aaccggggct aataccggat ggttgtttga accgcatggt tcagacataa     180
aaggtggctt cggctaccac ttacagatgg acccgcggcg cattagctag ttggtgaggt     240
aacggctcac caaggcgacg atgcgtagcc gacctgagag ggtgatcggc cacactggga     300
ctgagacacg gcccagactc ctacgggagg cagcagtagg gaatcttccg caatggacga     360
aagtctgacg gagcaacgcc gcgtgagtga tgaaggtttt cggatcgtaa agctctgttg     420
ttagggaaga acaagtgccg ttcaaatagg gcggcaccttgacggtacct aaccagaaag     480 ccacggctaa ctacgtgcca gcagccgcgg taatacgtag gtggcaagcg ttgtccggaa     540
ttattgggcg taaagggctc gcaggcggtt tcttaagtct gatgtgaaag cccccggctc     600
aaccggggag ggtcattgga aactgggaa cttgagtgca gaagaggaga gtggaattcc     660
```

-continued

```
acgtgtagcg gtgaaatgcg tagagatgtg gaggaacacc agtggcgaag gcgactctct      720
ggtctgtaac tgacgctgag gagcgaaagc gtggggagcg aacaggatta gataccctgg      780
tagtccacgc cgtaaacgtt gagtgctaag tgttaggggg tttccgcccc ttagtgctgc      840
agctaacgca ttaagcactc cgcctgggga gtacggtcgc aagactgaaa ctcaaaggaa      900
ttgacggggg cccgcacaag cggtggagca tgtggtttaa ttcgaagcaa cgcgaagaac      960
cttaccaggt cttgacatcc tctgacaatc ctagagatag gacgtcccct tcggggggcag    1020 agtgacaggt ggtgcatggt tgtcgtcagc tcgtgtcgtg agatgttggg ttaagtcccg     1080
caacgagcgc aacccttgat cttagttgcc agcattcagt tgggcactct aaggtgactg     1140
ccggtgacaa accggaggaa ggtggggatg acgtcaaatc atcatgcccc ttatgaacct     1200
gggctacaca cgtgctacaa tggacagaac aaagggcagc gaaaccgcga ggttaagcca     1260
atcccacaaa tctgttctca gttcggatcg cagtctgcaa ctcgactgcg tgaagctgga     1320
atcgctagta atcgcggatc agcatgccgc ggtgaatacg ttcccgggcc ttgtacacac     1380
cgcccgtcac accacgagag tttgtaacac ccgaagtcgg tgaggtaacc tttatggagc     1440
cagccgccga aggtgggaca gatgattggg gtg                                  1473
```